United States Patent [19]
Bell

[11] Patent Number: 6,165,504
[45] Date of Patent: Dec. 26, 2000

[54] METHODS FOR TREATING HOT FLASHES AND IMPROVING THE QUALITY OF LIFE OF CASTRATED PROSTATIC CANCER PATIENTS

[75] Inventor: Robert G. Bell, Palm Harbor, Fla.

[73] Assignee: Barr Laboratories, Inc., Pomona, N.Y.

[21] Appl. No.: 09/159,032

[22] Filed: Sep. 23, 1998

[51] Int. Cl.$^7$ ............... A61K 9/20; A61K 9/48; A61K 31/56

[52] U.S. Cl. ............ 424/464; 424/451; 514/178

[58] Field of Search .................. 424/451, 464, 424/489; 514/178

[56] References Cited

U.S. PATENT DOCUMENTS

| | | | |
|---|---|---|---|
| 3,234,093 | 2/1966 | Wiechert et al. | 167/74 |
| 3,895,110 | 7/1975 | Itil et al. | 424/242 |
| 4,738,957 | 4/1988 | Laurent et al. | 514/182 |
| 4,826,831 | 5/1989 | Plunkett et al. | 514/170 |
| 5,043,331 | 8/1991 | Hirvonen et al. | 514/170 |
| 5,135,849 | 8/1992 | Soto et al. | 435/29 |
| 5,595,985 | 1/1997 | Labrie | 514/169 |
| 5,610,150 | 3/1997 | Labrie | 514/170 |

OTHER PUBLICATIONS

Charig and Rundle, (Urology (1989) 18:175–178).
Froedin, T., The Prostate (1985) 7:203–208.
Kramer, P., et al., In: Murphy G., et al., 3rd Int'l Symposium on Recent Advances in Urological Cancer Diagnosis and Treatment—Proceedings.Paris, France: SCI:3–7 (1992).
Quella et al. (Urol. Nurs., 14(4):155–158 (1994)).
Loprinzi et al., (N. Engl. J. Med. (1994) 331:347–352).
Mosby's GenRx 1998, Megestrol Acetate.
Wehbe, et al., Mayo Clin. Proc. (Oct. 1997) 72:932–934.
Dawson et al. (J. Urol. (1995) 153: 1946–1947).
Mann, et al., Arch. Intern. Med. (Aug. 1997) 157: 1651–1656.
Bracci and Di Silvero, from Steffanine, P., et al., Proc. 18 World Cong. International Col. Surg. Rome 1972. Excerpta Med. (AMST), from International Cong. Ser. 290:275–276 (1972).
Goldenberg, S. L. et al., Pharmaceutical 1994, Current Perspectives on the Expanding Role of Androcur,® Pharma Libri Publishers Inc., p. 1–50.
The Androcur Monograph, Berlex, Canada (1977).
Claes H., et al., in Murphy GP (Prostate Cancer, Part A: Research, Endocrine Treatment, and Histopathology, New York, NY: Alan R. Liss (1987) 229–237.
Akakura, et al., Cancer 71: 2782–2790 (1993).
Hinkel et al., Eur. Urol. (1996) 30:464–470.
Rabe et al. (Drug Safety (1996(Jan.)); 14(1):25–38).
Eaton AC, McGuire N., Lancet (1983) 8363: 1336–1337.
Moon TD, Letter to the Editor. J. Urol. (1985) 134: 155–156.
De Voogt et al., J. Steroid Biochem. Molec. Biol. (1990)37(6): 965–969.
Goldenberg et al. (J. Urol. (1988) 140: 1460–1465).
Physians' Desk Reference, 35th Edition (1981) 1252–1257.
Lubeck DP, et al. Abstract of Qual. Life Res. Jul. 1997; 6(5):385–392.
Litwin, M.S., Abstract of Med. Care Jul. 1998; 36(7); 1002–1012.
Cella, DF: F.A.C.I.T. Manual, Version 4, Nov. 1997 (Center on Outcomes, Research and Education (CORE), Evanston Northwestern Healthcare And Northwestern University) Table of Contents and the following scales: FACT–G, FACT–P (two versions) and FACT–P–ES.
Esper et al. (Urology (1997) 50(6):920–928).
Clark, J.A. et al. Abstract of Soc. Sci. Med. (Oct. 1997); 45(8):1299–1309.
DiSilverio, et al., Eur. Urol. (1990) 18(suppl 3):54–58.
Thorpe et al., Eur. Urol. (1996) 29/1:47–54.
Miller et al. (Urology (1992)40(6):499–502.
Atala et al. (Urology (1992) 39(2): 108–110.
Cella, DF: J. Pain Symptom. Manage. (1994) 9(3):186–192.
Barradell, Lee, et al., Drugs & Aging, vol. 5(1):(1994) 59–80.
Gudziak, M., et al., West. J. Med. (1994) vol. 160(4):351.
Jansen, J.E., et al., Ugeskr laeger 151 (1989) 560–561.
Goldenberg, S., et al., Urology 47:882–884 (1996).
Bruchovsky, N., et al., Cancer Sep. 1, 1993, vol. 72, No. 5: 1685–1691.
El Etreby, M.F., et al., The Prostate 11: 361–375 (1987).
Cella, D., et al., portion of chapter 23 in Quality of Life and (unrecognizable) in Clinical (unrecognizable) Second Ed; ed. B. Spriker (1996) 203–205.
Rennie, P., et al., Abstract of Am. J. Clin. Oncol., Cancer Clin. Trials 1988 11/Suppl. 2(S13–S17).
Rennie, P., et al., Abstract of J. Urolo. 1988 139/6 (1337–1342).
Krause, W., et al., Abstract of Urol. Int. 1982 37/6 (400–409).

*Primary Examiner*—James M. Spear
*Attorney, Agent, or Firm*—Mark E. Waddell; Steve M. Haracz; Bryan Cave LLP

[57] ABSTRACT

A method for treating hot flashes in a castrated prostatic cancer patient who is diagnosed with hot flashes warranting treatment or who is experiencing at least approximately 5 hot flashes per day is provided in which from 25 mg to 150 mg cyproterone acetate per day is orally administered to the patient. A method for improving the multidimensional quality of life of such a patient is also provided. Palliative therapy for an advanced stage patient also improves quality of life.

31 Claims, No Drawings

METHODS FOR TREATING HOT FLASHES AND IMPROVING THE QUALITY OF LIFE OF CASTRATED PROSTATIC CANCER PATIENTS

FIELD OF THE INVENTION

The present invention relates to a treatment for surgically or chemically castrated prostatic cancer patients which alleviates hot flashes. The present invention also relates to a treatment for castrated prostatic cancer patients which improves the patients' quality of life.

BACKGROUND OF THE INVENTION

Surgical and chemical (LH-RH agonists) castration are widely used for the treatment of patients with prostate cancer. Apart from impotence, the most frequent long-term side effect of such therapy is the onset of distressing hot flashes (also known as hot flushes) similar to those seen in postmenopausal women. Vasomotor hot flashes and sweats occur in up to 80% of prostate cancer patients following either orchiectomy or treatment with LH-RH agonists. As many as one-third of these patients will experience persistent and frequent symptoms severe enough to cause significant discomfort and inconvenience. In one study in prostate cancer patients undergoing surgical castration, Charig and Rundle, (Urology (1989) 18: 175–178), found that 76% of their patients experienced hot flashes, and 30% believed their symptoms warranted treatment. In this study hot flashes started on average two to three months post-operatively and lasted in some patients for more than three years. However, the pattern in any individual patient was unpredictable. These results are in agreement with those of another study conducted in Sweden, as an attempt to quantify the degree of flashing by measuring skin blood flow and water evaporation. Froedin, T., The Prostate (1985) 7:203–208. The results of several other clinical trials reveal an incidence of hot flashes and sweats in about 40–80% of surgically or chemically castrated prostate cancer patients. One-third of all patients seek palliation and in many patients the symptoms may start as early as one to two weeks after castration.

Hot flashes can be extremely bothersome. They sometimes occur several times an hour, and they often occur at night. Hot flashes and outbreaks of sweats occurring during the night can cause sleep deprivation. Symptoms observed such as nervousness, fatigue, depression or inability to concentrate are considered to be caused by the sleep deprivation following night sweats. (Kramer, P., et al., In: Murphy G., et al., 3rd Int'l Symposium on Recent Advances in Urological Cancer Diagnosis and Treatment—Proceedings. Paris, France: SCI: 3–7 (1992)). Hot flashes can start without any warning. The attacks can last up to thirty minutes and vary in their frequency from several times a week to more than a dozen attacks per day. Hot flashes are associated with increased pulse rate. Generally, they are a source of great physical and mental stress to the prostate cancer patient. The vasomotor hot flashes often warrant medical treatment, yet a satisfactory treatment having few side effects has not been forthcoming.

The patient experiences a hot flash as a suddenly occurring feeling of heat which spreads quickly from the face to the chest and back and then over the rest of the body. These attacks are usually accompanied by outbreaks of profuse sweating. These external signs of the activation of heat loss by the body are associated with both dilatation of the cutaneous vessels and a decrease of the body temperature, which can be demonstrated as objective signs. Hot flash attacks are usually difficult to register because of their transient and unpredictable nature. However, in 13 castrated prostate cancer patients who reported hot flashes, Froedin et al. (The Prostate (1985) 7: 203–208), recorded a significant increase in cutaneous blood flow and in sweating by the use of a laser-Doppler flowmeter and an evaporimeter. The rate of evaporation increased synchronously with the increase in cutaneous blood flow. The intensity of the attacks as experienced by the patients corresponded closely to recorded measurements. Quella et al. (Urol. Nurs., 14(4): 155–158 (1994)) conducted a qualitative study to determine the level of severity of the hot flash. They found a noted consistency between what men considered as mild, moderate, severe, and very severe hot flashes. The authors proposed definitions of hot-flash severity, in accordance with their findings.

The symptoms of hot flashes have been rarely reported in prostate cancer patients treated with estrogens such as diethylstilbestrol (DES) or with cyproterone acetate (CPA) or megestrol acetate either alone or in combination with DES. There is no apparent difference in vasomotor hot flash response with respect to whether the primary therapy is surgical or chemical castration, or among patients receiving various formulations of different LH-RH agonists. Treatment with pure antiandrogens (such as flutamide) in addition to surgical castration or to LH-RH agonist treatment does not appear to significantly influence either the frequency or severity of hot flashes nor the response to treatment.

Estrogens such as DES may be effective to decrease hot flashes, but at the risk of gynecomastia and increased cardiovascular morbidity.

Megestrol acetate, a progestational hormone, has been shown to reduce hot flashes in men and women. A short term study reported by Loprinzi et al., (N. Engl. J. Med. (1994) 331: 347–352), indicated that low-dose megestrol acetate given to prostate patients who had undergone a surgical bilateral orchiectomy or treated with a gonadotropin-releasing-hormone agonist, reduced hot flashes by 50% in seventy-nine percent of the men in group 1 (those receiving megestrol acetate first) and in 12% of the men in group 2 (those receiving placebo first).

Megestrol acetate is indicated for the palliative treatment of advance breast and endometrium cancer and should not be used in lieu of surgery, radiation or chemotherapy. Weight gain associated with increased appetite is a frequent side effect of megestrol acetate. The drug is also indicated for the treatment of anorexia, cachexia, or a significant weight loss in patients diagnosed with AIDS. (Mosby's GenRx 1998, Megestrol Acetate.) Megestrol acetate has been shown to be effective therapy for metastatic prostate cancer. (Wehbe, et al., Mayo Clin. Proc. (October 1997) 72: 932–934, 932). Possible effects of low doses of megestrol acetate on the courses of hormonally sensitive tumors such as prostate tumors, are apparently unknown. See Loprinzi et al. (N. Engl. J. Med. (1994) 331: at 351).

Dawson et al. (J. Urol. (1995) 153: 1946–1947) show a paradoxical increase in prostate specific antigen (PSA) over time with megestrol acetate treatment as well as the marked increase in PSA after reinitiation of treatment with megestrol acetate in a patient with progressive metastatic prostate cancer. Dawson et al. also report a dramatic decrease in prostate specific antigen (PSA) after discontinuation of megestrol acetate. The case report concerned an orchiectomized prostatic cancer patient with metastatic disease who began megestrol acetate treatment during a period of tumor regression and stabilization. The condition remained stable for nearly two years. By that time, PSA reportedly increased from about 34 ng/ml to about 50 ng/ml, and then steadily increased over the next two months to about 110 ng/ml, when megestrol acetate was withdrawn. After PSA returned to about 40 ng/ml, reinitiation of megestrol acetate gradually caused an increase in PSA over the next three months to 149 ng/ml, at which time megestrol acetate was again discontinued. Wehbe et al. (Mayo Clin. Proc. (October 1997) 72: 932–934), reported a similar case. Stage IV metastatic prostate cancer was diagnosed in a patient with increased PSA levels. After initial treatment with leuprolide, the patient received megestrol acetate and continued hormone suppression with leuprolide. PSA levels reportedly decreased from 69 ng/ml to 31 ng/ml. By nine months after the start of treatment, however, PSA began a slow increasing trend, which later accelerated. By thirteen months after start of treatment, the PSA increased to 370 ng/ml (about a 12-fold increase), when megestrol acetate was discontinued. The PSA level then decreased over three months to 2 ng/ml, the substantial withdrawal decrease noted by the authors.

The Food and Drug Administration reported that evidence has been accumulating supporting the glucocorticoid activity of megestrol acetate in the patients who received it, most of whom were at an advanced stage of malignant disease. (Mann, et al., Arch. Intern. Med. (August 1997) 157: 1651–1656.) Cases of Cushing Syndrome were reported in women and diabetes mellitus and adrenal insufficiency associated with megestrol acetate were identified and reported in men and women. The exposure of patients with Cushing Syndrome to megestrol acetate was calculated to be 1440–20,000 mg×mo, whereas patients experiencing hyperglycemia generally had a lower exposure of 120–800 mg×mo. Patients with adrenal insufficiency had a wide range of exposure (from 90 to 32,000 mg×mo). Clinical complaints characteristic of adrenal suppression included nausea, vomiting, dizziness or hypertension, weight loss, or profound fatigue.

The use of megestrol acetate involves drawbacks in terms of an eventual dramatic increase in PSA for long-term use. It also appears that it should not be used intermittently, at least once PSA levels have notably increased and megestrol acetate has been withdrawn. Adverse effects associated with the glucocorticoid effects of the drug also may have a negative impact on quality of life of the patient.

It is generally thought that sudden reduction in the level of sex steroids precipitates hot flashes. The absence of hot flashes in aging men and the high frequency in postmenopausal women is believed to reflect the gradual change in male testicular function with age as compared with the abrupt reduction in female hormones at the menopause. The advanced age and hence reduced testosterone concentrations of men undergoing surgical or chemical castration for prostate cancer is thought to explain the absence of hot flashes in some patients after this treatment. In both sexes, hot flashes are usually associated with clinical situations which can most appropriately be defined as acquired gonadal insufficiency. This applies to the situation of prostate cancer patients after surgical castration and under LH-RH agonist therapy, as well as to women after the menopause. In all cases, the occurrence of hot flashes is preceded by a marked sudden decrease of previously normal levels of sex steroid.

Normal endocrine regulation in the hypothalamus involves a negative feedback mechanism in which the sex steroid levels influence LH-RH release, i.e., high sex steroid levels reduce LH-RH release and vice versa. These opposing influences are mediated via two intermediate components—inhibitory opioids and stimulatory catecholamines. When the sex steroid level is low, for example, a smaller amount of opioid-peptides is released, leading to an increase in the catecholamine concentration and, consequently, the increased release of LH-RH.

A possible characterization of the intrahypothalamic situation in patients suffering from hot flashes is that it is accompanied by a decrease of inhibitory opioids, an increase of catecholamines (adrenergic activity) and increased LH-RH release. Catecholamines such as norepinephrine are involved in the physiological regulation of body temperature. In view of the close anatomical relationship between the thermoregulatory center and the LH-RH neurons, an increase in the intrahypothalamic concentration of catecholamines stimulates not only the LH-RH secreting neurons, but also the neurons involved in thermoregulation, i.e., "the watering can effect". This stimulation leads to activation of heat loss, which manifests itself clinically as a hot flash. Vasomotor hot flashes and sweats can thus occur as a result of a disturbance of thermoregulation.

Opioids are indirectly involved in the genesis of hot flashes via the absence of their inhibitory effect on the release of catecholamines. In contrast, the increased release of LH-RH apparently plays no role in the induction of hot flashes as it occurs as a result of the increased concentration of catecholamines. The reduction of the testosterone level secondary to orchiectomy provokes a counter-regulatory effect with an intrahypothalamic increase of adrenergic activity, from which hot flashes result. The same applies to medical castration with LH-RH agonists. The occurrence of hot flashes is not prevented by additional administration of pure antiandrogens, since these substances have no inhibitory effect on the increased adrenergic activity in the hypothalamus.

Cyproterone acetate ("CPA") is disclosed in U.S. Pat. No. 3,234,093, which is incorporated herein by reference. CPA, a synthetic 21-carbon hydroxyprogesterone derivative, is a steroidal antiandrogenic agent that inhibits the action of adrenal and testicular androgens on prostatic cells, resulting in total androgen blockade. Additionally, due to the antigonadotropic effects of its progestogenic activity, CPA causes a centrally mediated reduction in testicular secretion of androgens. CPA is approved for use in many countries throughout Europe, Asia, Australia, South America and Canada. It is used as a component of oral contraceptives and in the treatment of acne, seborrhea, hirsutism, precocious puberty, hypersexuality and in the treatment of prostate cancer. The pharmaceutical preparations Androcur®, Cyprostat®, Diane®, Dianette® are CPA-based products. Manufacturers of these products include Schering AG, Berlin, Germany and Berlex, Canada.

Since 1966, CPA has been used in combination with bilateral orchiectomy to achieve total androgen blockade in the treatment of prostate cancer. CPA has also been administered as monotherapy for prostate cancer. Dosages of 250–300 mg/day are used to bring about a complete antiandrogenic blockade. Dosages prescribed are usually 200–300 mg/day, divided into 2–3 doses. After orchiectomy a lower daily dose of 100–200 mg may be recommended. In a study reported in 1972 by Bracci and Di Silvero (discussed in Goldenberg, S. L. et al., Pharmanual 1994, Current Perspectives on the Expanding Role of Androcur,® Pharma Libri Publishers Inc., p. 23–24), CPA was administered at 100 mg/day or more with orchiectomy to patients with various advanced tumors for more than 2 years. The investigators noted that CPA in combination with orchiectomy has marked therapeutic effectiveness.

Side effects most frequently recorded with CPA treatment relate to the hormonal effects of the drug. These include impotence, inhibition of spermatogenesis and gynecomastia. These reactions are usually reversible upon discontinuation of therapy or reduction in dose. The drug is also associated with rapid falls in serum testosterone levels, which may also produce such central nervous system effects as fatigue, weakness, and headache.

Unlike other androgen deprivation therapies, CPA is rarely associated with hot flashes. Prostate cancer patients receiving CPA combined with surgical or chemical castration are less likely to experience hot flashes than those who do not receive CPA. (Barradell et al., Drugs & Aging (1994) 5/1:59–80.) CPA has a low incidence of side effects and its antigonadotropic and antiandrogenic effects are reversible, which enables intermittent therapy. CPA also has the added benefit of being "cancerocidal" to prostate cancer cells due to its potent antiandrogenic activity.

Another beneficial effect seen with CPA treatment has been the prevention of exacerbated bone pain. Patients with Stage C and D prostate cancer indicated improvement in bone pain with CPA as monotherapy. (Barradell et al., Drugs & Aging (1994) 5/1: 59–80). Overall, pain relief has been noted in 50–80% of patients receiving treatment with ANDROCUR®. (The Androcur Monograph, Berlex, Canada (1997)). The effect of CPA on pain generally paralleled its effect on metastasis. Id. When metastasis remained improved or stabilized, the analgesic requirement was also reduced. Id.

It has also been reported that exacerbated bone pain associated with the flare reaction at the start of LH-RH agonist treatment is prevented with CPA administered to prevent acute flare-up of prostatic disease. The Goldenberg, S. L. et al., Pharmanual cited above, indicates that Claes H., et al., in Murphy GP (Prostate Cancer, Part A: Research, Endocrine Treatment, and Histopathology, New York, N.Y.: Alan R. Liss (1987) 229–236), found that 58.5% of 17 patients who received goserelin alone experienced a transient increase in bone pain compared with none of 7 patients who received goserelin acetate plus 200 mg/day CPA. For the short-term prevention of tumor flare, CPA has been administered with an LH-RH agonist generally at 150 to 300 mg/day dosages. Also for tumor flare, CPA has been administered at 100 mg/day in combination with 0.1 mg/day DES. (Bruchovsky et al., Cancer 71: 7282–2790 (1993)).

The Androcur® Monograph, Berlex Inc., Canada (1997), indicates a general improvement in the subjective assessment of the quality of life in 70% of 367 evaluable patients participating in worldwide studies on CPA, based on criteria of general improvement in quality of life. The criteria listed are weight gain and pain relief. The patients considered included ones who received CPA as monotherapy, an estrogen refractory group, and orchiectomized patients. It appears that dosage forms included oral and i.m. injection and that the doses varied. Most patients who received oral CPA were dosed at 200 to 300 mg/day. The lowest oral dose possibly given to orchiectomized patients was indicated to be 100 mg/day. The data provided indicate the percent of patients in each of the three patient groups with complete or partial remissions. For previously untreated patients, Androcur® treatment resulted in 50% remission; for estrogen refractory patients, Androcur® treatment resulted in 44% remission; for orchiectomized patients, Androcure patients had a 60% remission. There is no indication of percent improvement subjectively assessed by group or by dosage administered.

Dose-related hepatic toxicity in humans has been reported with the prolonged use of CPA. Toxicological studies have revealed, however, that administration of CPA to humans does not pose a serious risk of hepatotoxicity. A retrospective liver toxicity analysis was performed on 89 patients with advanced prostatic cancer who underwent orchiectomy and who received continuous additional antiandrogenic treatment with 50 mg/day CPA. (Hinkel et al., Eur. Urol. (1996) 30:464–470). CPA was administered to these patients for a period spanning from 2 to 152 months starting at the time of diagnosis. Various medications were frequently prescribed besides CPA treatment. Although a proper control group was lacking, in no case was CPA discontinued due to its side effects. After evaluating the patients' liver function, the authors concluded that CPA is a reliable drug to inhibit androgen synthesis with maximum efficacy and safety in the treatment of prostate cancer.

Moreover, a thorough review on the toxicology of CPA was published by Rabe et al. (Drug Safety (1996 (Jan.)); 14(1):25–38). In a multi-center surveillance study of long term CPA use in over 2500 patients, the treatment group included men and women. The men were treated at dosages of either more than 200 mg/day or from 100 to 200 mg/day CPA. No correlation was found between the duration of CPA treatment and the prevalence of liver enzyme elevations. Not a single case of hepatocellular carcinoma was observed. The authors concluded that there were no observations that would indicate an increased risk of proliferative liver change as a result of CPA treatment.

The minimum dosage of CPA for an antigonadotropic effect in men may not be precisely known. The threshold value for an antiandrogen effect in men was indicated to be 50 mg according to U.S. Pat. No. 3,895,110, which issued in 1975. Presumably then, the threshold value for an anticancerocidal dosage in prostate cancer patients may also be 50 mg. Blood levels of CPA are known to be generally dose dependent.

In a double-blind, crossover trial, Eaton and McGuire treated 12 prostate cancer patients with troublesome post-orchiectomy hot flashes with CPA or placebo. (Eaton AC, McGuire N., Lancet (1983) 8363: 1336–1337). They reported that the frequency of hot flashes was significantly reduced during the three weeks that CPA (100 mg three times daily) was given. The 1994 Barradell et al. review article cited above summarizes the Eaton et al. data as reducing hot flashes from a mean number of 9.44 per day before CPA treatment to 2.26 per day after the 21 day treatment period. Five patients complained of lassitude while on this regimen. In one patient the lassitude was reportedly severe. The dosage of CPA was reduced to 100 mg/day for this patient and it was stated to completely suppress vasomotor symptoms without side effects. The article provides no indication of a "wash-out" period between dosages or of how long this single patient was administered 100 mg CPA daily before this observation was made.

Bruchovsky et al. (Cancer 71: 2782–2790 (1993)), report administration of 100 mg/day CPA in combination with 0.1 mg/day DES to eliminate the flare reaction encountered upon the first administration of LH-RH agonist. CPA treatment was then maintained to reportedly suppress vasomotor symptoms, citing the Eaton paper. The dosage administered was increased in some patients.

Moon reported anecdotal evidence of the efficacy of CPA in the treatment of hot flashes. (Moon T D, Letter to the Editor. J. Urol. (1985) 134: 155–156). A patient who underwent orchiectomy for metastatic carcinoma of the prostate had been troubled with 10 to 15 hot flashes daily. These episodes lasted only a few minutes but they were bothersome and accompanied by marked facial sweating. Treatment with estrogens was contraindicated because of angina and a previous myocardial infraction. This patient was treated initially with 100 mg CPA three times a day and a good response was obtained. The drug was then discontinued and the hot flashes increased during the next few weeks and were back to pre-treatment numbers by four weeks. CPA was then administered at 50 mg two times per day. Moon stated that there was a significant reduction in the number of hot flashes and that the severity of the remaining hot flashes was much reduced in this patient.

Noting the importance of a large scale randomized clinical trial in view of a considerable placebo effect reported in the treatment of hot flashes in menopausal women, Kramer et al., cited above, reported in 1992 a trial of 273 patients treated with CPA who had previously undergone orchiectomy and who had the mere occurrence of hot flashes and/or outbreaks of sweat. The investigators chose 150 mg/day CPA (50 mg t.i.d.) as their treatment dose. After six months of treatment with CPA the number of patients experiencing hot flashes or outbreaks of sweating decreased as compared with placebo. Hot flashes were reportedly experienced by 33% of patients receiving CPA and 61% of patients receiving placebo, while 24% of CPA-treated patients had outbreaks of sweating compared with 47% of placebo-treated patients. Although no data were provided, in those patients receiving CPA who continued to experience hot flashes or sweating, the frequency and severity were stated to be strongly reduced.

In several randomized well-controlled clinical trials in prostate cancer patients, if CPA was given in combination with LH-RH agonists such as Zoladex®, or Buserlin®, there was a reduction in the percentage of patients reporting hot flashes. (De Voogt et al., J. Steroid Biochem. Nolec. Biol. (1990) 37: 965–969; DiSilverio, et al., Eur. Urol. (1990) 18 (suppl 3): 54–61; Thorpe et al., Eur. Urol. (1996) 29/1:47–54.) A 1994 review article by Barradell L B, et al. (Drugs & Aging (1994) 5/1: 59–80), summarized that while no studies have been done objectively assessing quality of life per se, the effect of CPA used at dosages of 150 to 300 mg/day on the incidence of hot flushes has been favorable for patients undergoing pharmacological or surgical castration.

U.S. Pat. No. 3,895,110 to Itil et al. (which issued in 1975) disclosed the treatment of psychic disturbances of the affective or behavioral type within a broad potential dosage range of CPA. The Itil patent recommends, however, treating at a dosage of CPA under the threshold value for an antiandrogen effect in both men and women. The Itil patent reports significant remission of premenstrual anxiety and tension conditions in women. A study on five males suffering from symptoms of anxiety characterized by nervousness, restlessness, anxiety, headache, and tachycardia, treated with 1 to 6 mg CPA daily for 2 weeks, was also reported. The Itil patent indicates that the results in the men were mixed. Moreover, in one patient showing moderate improvement at 3 to 4 mg per day, an increased dosage resulted in restlessness in the patient.

Goldenberg et al. (J. Urol. (1988) 140: 1460–1465) reported that CPA and low dose DES may be co-administered to achieve a synergistic androgen withdrawal effect in the treatment of advanced prostatic carcinoma. CPA administered at 200 mg/day with 0.1 mg daily DES showed a marked decrease in serum testosterone, with no change upon decreasing CPA to 100 mg/day in the combination. In a subsequent report, Goldenberg et al. (Urology 47 (6) (1996) 882–884) indicate that 100 mg CPA and 0.1 mg DES per day result in persistent decrease in serum testosterone with a lower incidence of side effects than the 200 mg/day CPA combination. Bruchovsky et al. (Cancer 71: 2782–2790 (1993)) report elimination of flare reaction by pretreatment with CPA and low-dose DES. Patients were pretreated with 100 mg per day CPA and 0.1 mg/day DES for 4 weeks. Goserelin acetate was then given and CPA/DES was continued. DES administration was discontinued at 8 weeks to eliminate associated minor toxicity. Both Goldenberg et al. articles report that during the administration of CPA and DES in combination, hot flashes/night sweats were incident in 8% of patients.

Goldenberg et al. (J. Urol. (1988) 140: 1460–1465) indicate that the weakening of the antigonadotropic effect of CPA, seen after 6 to 9 months, was not observed with the continued co-administration of DES.

It has also been forwarded that estrogens may increase prostatic cancer growth. In the treatment of prostate cancer, U.S. Pat. No. 5,610,150 discloses a combination therapy for prostate cancer treatment that includes an antiantrogen, a sex steroid biosynthesis inhibitor and an antiestrogen for the prevention of the biosynthesis of estrogen.

Estrogens have been shown to be effective in the treatment of hot flashes. Conjugated estrogens such as Premarin® are indicated for the treatment of vasomotor hot flashes in menopausal women.

Estrogens also have a testosterone-reducing effect that is based to a large extent on the increased release of inhibitory factors from the hypothalamus in addition to a direct effect on the pituitary gland. As a result, it is thought that the occurrence of intrahypothalamic counter-regulation of catecholamines (adrenergic activity) is impeded and the disturbance of thermoregulation prevented.

Miller et al. (Urology (1992) 40: 499–502) report treating 12 prostate cancer patients suffering from severe symptoms of post-orchiectomy hot flashes and sweats with 0.33 mg DES daily. Nine patents demonstrated both objective and subjective improvement in symptoms. Five patents experienced adverse drug reaction including onset of gynecomastia. Atala et al. (Urology (1992) 19: 108–110) report that of bilateral orchiectomy patients reporting vasomotor symptoms, the frequency and severity of hot flashes were significantly reduced during the time 1 mg/day DES was given.

Chlorotrianisene, an estrogen which was sold in the United States under the name TACE®, was indicated for the palliative therapy of advanced prostatic carcinoma and for moderate to severe vasomotor symptoms associated with the menopause, among other things. For long-term treatment of progressive prostatic cancer, 12 mg to 25 mg daily was prescribed. For cyclic short term use in women to treat severe vasomotor symptoms, the same dosage amount was usually prescribed. (Physicians' Desk Reference, 35th Edition (1981).

There remains no suitable treatment for vasomotor hot flush in surgically or chemically castrated prostatic cancer patients. A method for treating hot flashes and sweats that accompany androgen ablation therapy of prostate cancer has long been desired and will fulfill an important medical need.

SUMMARY OF THE INVENTION

The present invention provides a method for treating hot flashes in a castrated prostatic cancer patient by orally administering from 25 mg to 150 mg cyproterone acetate per day, preferably from 50 mg to 100 mg CPA per day. The present method provides a reduction in number of hot flashes. It is recognized that the method is effective for patients experiencing as many as at least 5 hot flashes per day or for patients diagnosed with hot flashes warranting treatment. Treatment is for at least a time sufficient to alleviate the hot flashes. Treatment is generally provided for at least 60 days, preferably for at least 9 to 12 months. Intermittent therapy is also contemplated.

Hot flashes as well as other effects of the cancer treatments that these patients receive, adversely affect the quality of life of the patients. Patients are treated with CPA for at least a time sufficient to improve the patients' quality of life. Quality of life can be measured and improvement shown by an increase in score of at least 5 points on the FACT instrument, e.g., the FACT-P instrument or a modified version.

The present invention also provides a method of treating castrated prostatic cancer patients with 25 mg to 150 mg cyproterone acetate per day in combination with a low dosage estrogen to treat hot flashes and/or to improve the patients' quality of life.

DETAILED DESCRIPTION OF THE INVENTION

The incidence and severity of hot flashes were confirmed in a survey conducted with prostate cancer patients. The patients had received various treatments such as prostatectomy, orchiectomy, and chemical treatments, the majority with Lupron®, Zoladex®, Eulexin®, or Casodex®. All of the patients surveyed that had undergone surgical or chemical castration had hot flashes, and 60% of these patients experienced hot flashes several times a day. Over 53% of the patients surveyed felt that hot flashes have affected their quality of life (quality of life was defined as the patients' perception of their performance in physical and occupational function, psychological state and social interaction). 12% of patients polled were taking Deprovera®, Megace®, Clonidine® or antihistamines for their hot flashes. 44% were not satisfied with the results of this medication. In addition, 64% of the patients surveyed would request treatment for the hot flashes if a medication were available.

The survey asked the patients to rate their hot flash severity among categories which are generally in accordance with the definitions of hot flash severity provided by Quella et al., cited above. The questionnaire provided a choice among the following category definitions of hot flash severity in a male cancer patient:

Mild—Duration:<3 minutes; Physical Symptoms: very light perspiration, generalized warmth or a flushed sensation; Emotional Symptoms: none or rare; Action needed: usually no action taken.

Moderate—Duration:$\leq 5$ minutes; Physical Symptoms: light to moderate perspiration, moderate warmth and/or perspiration; Emotional Symptoms: mild anxiety, some irritability, loss of concentration; Action needed: needed to use a fan, needed to loosen clothing, needed to remove clothing, needed to remove bedding.

Severe—Duration:$\leq 10$ minutes; Physical Symptoms: described as feeling "hotter" or "very hot", heavy perspiration, nausea, weakness, dizziness, shortness of breath, extreme discomfort; Emotional Symptoms: moderate anxiety, moderate irritability; Action needed: needed to loosen clothing, needed to change clothing, needed to change bedding.

Very Severe—Duration:$\leq 30$ minutes; Physical Symptoms: described as feeling "very hot", drenching perspiration, nausea, weakness, dizziness, shortness of breath, chest discomfort, extreme discomfort; Emotional Symptoms: severe anxiety, severe irritability, restlessness, totally out of control; Action needed: needed to change clothing, needed to towel off, needed to change bedding, used wet towels, took a bath or shower, needed a rest.

Most patients rated the severity of their hot flashes as being moderate most of the time (45% of patients). 39% of patients rated their hot flashes as mostly mild, 16% as mostly severe, and 2% as very severe most of the time.

Castrated prostatic cancer patients, in accordance with the present invention, are those prostate cancer patients who have undergone surgical castration, e.g., bilateral orchiectomy, or who have undergone or are undergoing chemical or medical castration, e.g., by administration of an LH-RH agonist such as Lupron® or Zoladex®. These patients can additionally be undergoing or have undergone pure antiandrogen treatment such as with flutamide. The patients can be undergoing other treatments, as long as administration of CPA therewith is approved by the patients' physicians or otherwise not contraindicated.

In accordance with the present invention, chemically or surgically castrated prostatic cancer patients are treated for vasomotor hot flushes with CPA in an amount of from 25 mg to 150 mg CPA per day in an oral dosage form. Preferably, the dosage used is from 50 mg to 100 mg CPA per day. Castrated prostatic cancer patients experiencing bothersome hot flashes who seek to reduce the number and/or severity of their hot flashes, i.e., to alleviate hot flash symptoms, are candidates for treatment. Castrated prostatic cancer patients having elevated catecholamines resulting in a disturbance in thermoregulation are also candidates.

Preferably, CPA is administered at a dosage and for a time such that the number of hot flashes is reduced as compared to the number of hot flashes prior to the start of CPA treatment. Such treatment can also be beneficial to reduce the overall severity or intensity distribution of any hot flashes still experienced, as compared to the severity of hot flashes prior to the start of CPA treatment. Moreover, treatment is preferably such that hot flashes become less frequent and hot flash score as defined below is reduced. Most preferably, treatment is at a dosage and for a time in accordance with the present invention such that a substantial elimination of hot flashes results.

For example, CPA can be administered to a castrated prostatic cancer patient who experiences any number of hot flashes per day. For a patient who experiences approximately 3 hot flashes per day, for example, it is recognized that a dosage of from 25 mg to 150 mg CPA per day can be administered for a time such that the number of hot flashes is reduced or such that hot flashes are substantially eliminated.

In particular, it is recognized that CPA administered at a dosage amount in accordance with the present invention to castrated prostatic cancer patients experiencing many hot flashes, e.g., as many as approximately 5 hot flashes per day or more, is effective to produce a sufficiently significant result in teens of a decrease in the number of hot flashes they experience and preferably in the severity of any hot flashes remaining. These patients who are treated with 25 mg to 150 mg CPA per day can advantageously achieve alleviation or elimination of vasomotor hot flash symptoms. Patients having an average of about 60 hot flashes per week can also benefit. Moreover, it is recognized that treatment with CPA at a dosage amount in accordance with the present invention to castrated prostatic cancer patients diagnosed by a physician with hot flashes warranting treatment can also be effective to produce a sufficiently significant result in terms of a decrease in the number of hot flashes they experience.

Reductions in the number and possibly the severity of hot flashes in patients experiencing at least approximately 5 hot flashes per day or diagnosed with hot flashes warranting treatment can be suitable in the treatment ranges of from 25 mg to 100 mg CPA per day. It is also recognized that these dosages can result in a sufficiently significant result, although they provide generally lower blood concentration of CPA. The preferred dosages are from 50 mg to 100 mg CPA per day.

An approximate number of hot flashes is about the average number of hot flashes experienced over the few days before the start of CPA administration, e.g., over the last three to five days. It could also be about the average number over a longer span of time before the start of administration, e.g., over about twelve weeks. The overall severity distribution of hot flashes is the approximate percentage of hot flashes a patient has in each severity category. A reduction in the severity of hot flashes a patient experiences upon CPA treatment occurs when a greater percentage of hot flashes are characterized into lower severity categories than in the severity distribution prior to treatment.

A hot flash score is a value that represents the number of hot flashes multiplied by the severity or intensity of the hot flashes. As described by Loprinzi et al. cited above, the hot flash score for a patient is calculated by adding the total number of mild hot flashes, twice the number of moderate hot flashes, three times the number of severe hot flashes, and four times the number of very severe hot flashes experienced in a given day. For an average hot flash score, the number of hot flashes for a number of days can be added and calculated as above, and then divided by the sum of the number of days for which values were included.

A dosage which provides a sufficiently significant result in accordance with the present invention is one which preferably reduces the number of hot flashes experienced in a patient who has at least approximately 5 hot flashes per day by more than one hot flash per day. Such a dosage can of course, be administered to patients who experience fewer than 5 hot flashes per day.

Preferably, and not necessarily, a dosage which provides a sufficiently significant result in terms of the reduction in number of hot flashes mentioned also reduces the overall severity distribution of any remaining hot flashes. A measure which represents a composite value that takes into account a reduction in number as well as in severity of hot flashes is a reduction in the hot flash score of the patient. Preferably, a dosage of CPA in accordance with the present invention is administered for a duration such that the hot flash score is reduced as compared to the score prior to treatment. More preferably, hot flash score decreases by at least about 20% of the score prior to CPA treatment.

It is recognized that typically the hot flash score will reflect a reduction in both the number and severity of hot flashes. A dosage which may not meet the criteria for a sufficiently significant result in terms of a reduction in number of hot flashes as set forth above, may alternatively meet the definition by about a 20% reduction in hot flash score in which the reduction in severity compensates for the reduction in number. More preferably, CPA is administered at a dosage and for a time sufficient such that the patient has a reduction in hot flash score of greater than 20% of the score prior to CPA treatment.

It is recognized that patients experiencing an approximate number of from 5 to 25 or more hot flashes per day, e.g., 29 per day, can surprisingly achieve significant alleviation or substantial elimination of vasomotor hot flash symptoms with the present treatment. Moreover, it is recognized that patients experiencing at least approximately 5 hot flashes per day, most of which are rated from moderate to severe, who are treated with CPA in accordance with the present invention, can achieve a significant lessening in the overall severity of their hot flashes.

Administration of CPA may continue for at least as long as is sufficient to achieve a reduction in the number of hot flashes and preferably also in the severity of any remaining hot flashes. For example, CPA can be administered to a patient having hot flashes rated as mostly mild in severity until the patients' hot flashes are substantially eliminated. Also for example, CPA can be administered to a patient having hot flashes rated as mostly moderate in severity before treatment until most of any hot flashes experienced during CPA treatment are rated as mild.

It is also notable that hot flashes having a severity level of at least moderate in accordance with the guidelines provided are accompanied by emotional symptoms of varying degrees of anxiety and irritability. CPA treatment that results in reduction in the severity of hot flashes in a patient having at least moderately sever hot flashes can thus be considered to reduce the severity of the emotional symptoms accompanying the hot flashes.

Generally, the treatment term is for sixty days or longer, e.g., about 180 days. It is preferable that the patient be administered CPA for at least 180 days. A period of at least 6 months, e.g., at least 9 months, is desirable. A preferred length of treatment is from 9 to 12 months. Treatment can also be for greater than 12 months. Administration can be for as long as 2 years or more, e.g., from 2 to 3 year, since CPA administered according to the present invention is well tolerated long-term. This is important because patients may survive for many years after their diagnosis.

The treatment term can be continuous or intermittent, preferably at the discretion of the physician and/or the patient under a doctor's supervision. Treatment is preferably continuous, i.e., CPA is taken every day. Continuous treatment is preferably for at least 60 days, e.g., about 180 days, more preferably for at least 6 months.

For intermittent therapy, after a period of treatment the patient withdraws from taking the drug for a length of time, and then resumes taking the drug as desired when hot flashes or other symptoms return to an uncomfortable level. Preferably, the patient resumes taking the drug before this point is reached. As a guideline for intermittent treatment, the patient can take CPA continuously for more than 30 days immediately before a period during which no CPA is taken. The time during which the patient then does not take CPA generally does not exceed about 30 days. Administration is preferably continuous for at least sixty days from the start of CPA treatment and then can be intermittent at some time thereafter. Optimum treatment will vary from patient to patient.

Patients with progressive medical illnesses, including those with cancer, experience numerous symptoms, impairments in physical and psychosocial functioning, and other problems that can undermine the quality of life. Quality of life reflects perceived well-being and relates to many diverse positive and negative phenomena. Quality of life has two overriding characteristics: subjectivity and multidimensionality. Cella, D F: J. Pain Symptom. Manage. (1994) 9:186–192.

The inherent subjectivity of quality of life has implications for assessment. Although clinicians commonly make inferences about patients' well being, the likelihood of inaccuracy in such appraisals must be appreciated. Inferences made by clinicians about subjective states may be particularly uncertain at a level of patient distress that is most clinically relevant. For the evaluation of hot flashes and pain, for example, patient self report is important.

Quality of life as addressed in the present invention is a multidimensional phenomenon. Many factors or aspects are taken into consideration which include the physical, psychological and social dimensions as well as what are generally more personal considerations which could be characterized as spiritual/existential dimensions. Although more difficult to characterize, these latter aspects are clinically prominent. In addition to hot flash and pain assessments, aspects of quality of life that are relevant to the patient and family are explored. Patient self report is critical with regard to these dimensions of quality of life.

Moreover, questions put to the patient that screen for disturbances are useful in clarifying the depth to which each dimension should be explored.

Quality of life indicia for prostatic cancer patients encompasses the status of the medical condition as manifested by symptoms, functional capacity, psychological state and self perception, and includes ability to interact socially, work performance, urinary and sexual function, and life satisfaction. The patients' experiences of pain and hot flashes are considered, but are by no means exclusive considerations. All of the quality of life indicia are taken into consideration with regard to the patients' subjective assessment of them, to obtain an overall objective indication of a multidimensional quality of life. In order to determine the effect of treatment on the patient group, a multidimensional quality of life assessment is made before orchiectomy or before the start of treatment with a chemical castrating agent, during and/or after treatment in the case of castration with a chemical agent, and after treatment in the case of orchiectomy. The objective quality of life determinations before and after treatment can then be compared.

There are several validated instruments that can be used as tools to assess the multidimensional aspects of quality of life. These include the Spitzer UNISCALE for Overall Quality of Life, Cleeland's Brief Pain Inventory (BPI) Global Question, a modified UNISCALE pertaining to the effect of hot flashes on patient quality of life and the FACIT measurement system.

Lubeck D P, et al. (Qual. Life Res. July 1997; 6(5) :385–392) report good reliability and validity of an instrument for assessing health-related quality of life (HRQOL) in CaPSURE (Cancer of the Prostate Strategic Urologic Research Endeavor). The instrument includes the UCLA Prostate Cancer Index, the RAND 36 item Health Survey 1.0 and items addressing self-esteem and the impact of prostate cancer in general and on the family. The UCLA Prostate Cancer Index was developed to provide an accurate measure of health-related quality of life (HRQOL) in men treated for prostate cancer. (Litwin, M.S., Med. Care July 1998; 36(7); 1002–1012). The authors were particularly interested in health concerns central to the quality of life of men treated for early stage prostate cancer. The targeted items address impairment in the urinary, bowel and sexual domains.

Perhaps the instrument best suited for assessing the quality of life in prostate cancer patients is the FACIT Measurement System. Cella, DF: F.A.C.I.T. Manual, Version 4, November, 1997 (Center on Outcomes, Research and Education (CORE), Evanston Northwestern Healthcare And Northwestern University). The FACIT system (Functional Assessment of Chronic Illness Therapy) is a collection of quality of life questionnaires targeted to the management of chronic illness. This is an expansion of the FACT (Functional Assessment of Cancer Therapy) series of questionnaires aimed at assessing chronic illnesses and conditions, first developed in 1987. The core questionnaire consists of a 27-item compilation of general questions divided into four primary quality of life domains: physical well-being, social/family well-being, emotional well-being and functional well-being. Questions relating to the patients' relationship with the doctor are also included. This FACT-G (Functional Assessment of Cancer Therapy-General) instrument is considered appropriate for use with patients with any form of cancer. A scaled response from zero to 4 is requested indicating how true each statement has been for the patient over the past 7 days, with zero representing "not at all" and with 4 representing "very much." It will be noted that the scoring guide for the questionnaire identifies negatively stated items for which the score must be reversed before adding scores to obtain subscale totals.

Under the category of physical well-being, the types of statements that the questionnaire asks the patient to rank include, for example, "I have pain", as well as other statements such as "I am bothered by the side effects of treatment" and "Because of my physical condition, I have trouble meeting the needs of my family." Under the category social/family well-being, the statements include, for example, "I get emotional support from my family" and "I feel close to my partner (or the person who is my main support)." Under the emotional well-being category, statements for ranking include, for example, "I feel nervous," "I feel sad" and "I worry that my condition will get worse." Under the category of functional well-being, the questionnaire includes, for example, "I am able to work (include work at home)", "I am able to enjoy life," and "I am sleeping well." These are examples of questions exploring the different aspects of quality of life, all of which require the patient's subjective assessment.

Validation of the core FACT-G instrument allowed for the evolution of subscales targeted to specific treatment groups. FACIT subscales have been developed to compliment the FACT-G, addressing relevant disease, treatment or condition-related issues not covered in the general questionnaire. Each is intended to be as specific as necessary to capture the clinically relevant problems associated with a given condition or symptom, yet general enough to allow for comparison across diseases, and extension, as appropriate, to other chronic medical conditions. Celia, D F: F.A.C.I.T. Manual, Version 4, November, 1997. Each disease-specific questionnaire includes the FACT-G subscales in addition to the disease-specific subscale.

Validated subscales exist for prostate cancer patients and for patients with endocrine symptoms. The prostate-specific subscale is known as the prostate cancer subscale. ("PCS"). This subscale in addition to the FACT-G subscales is known as the FACT-P. The endocrine symptom-specific subscale in addition to the FACT-G is known as the FACT-ES. The FACT-P rating scale, set forth in its entirety by Esper et al. (Urology (1997) 50(6): 920–928), which is incorporated herein by reference, includes "prostate specific" questions. Use of the FACT-P instrument has been accepted as a validated tool to measure and report quality of life in men with prostate cancer. In fact, a significant correlation was reported between prostate specific antigen level and certain of the FACT-P subscales. The statements that the PCS questionnaire requests the patient to rate include issues of change in weight, appetite, urinary function, sexual function, and pain, all aspects being subjectively assessed by the patient. Particular statements include, for example, "I have aches and pains that bother me", and "My pain keeps me from doing things I want to do."

The FACT-P instrument is a preferable instrument to use as a tool to assess the quality of life of a prostatic cancer patient. The FACT-P instrument can preferably be modified by the addition of questions from the FACT-ES pertaining to hot flashes that are also highly relevant to the quality of life of castrated prostatic cancer patients. Such added questions can inquire, for example, with regard to hot flashes, night sweats and cold sweats and ask for an assessment of whether hot flashes are affecting quality of life.

The FACT instrument can further be supplemented with one or more simple visual analogue measures of important aspects of quality of life relative to the potential changes in quality of life encountered by castrated prostate cancer patients. The use of simple single-item visual analogue measures to supplement longer instruments has long been established. Three constructs which are recognized as useful in conjunction with the FACT instrument are: 1) the overall quality of life a patient reports in taking all multidimensional aspects of quality of life into consideration; 2) the degree to which hot flashes affect the patient's overall quality of life; and 3) the amount of pain experienced and pain reduction achieved.

The first construct can be asked of the patient in the form of the Spitzer UNISCALE for overall quality of life. This was one of the first quality of life tools developed (1981) and has been used extensively in various clinical trial settings. Its primary advantage lies in its simplicity as a single item visual analogue measure. Because the scale asks for a multidimensional assessment, this quality of life tool can be used as an exclusive measure, if desired.

The second construct, the degree to which hot flash activity affects overall qualify of life, can be addressed by a modified UNISCALE format single item that asks this question specifically in a visual analogue format. Cleeland's Brief Pain Inventory (BPI) global question, a useful instrument for measuring patient pain, can be used to obtain information regarding the third construct. Developed as a battery of individual items, elements of the BPI can be extracted and used separately as desired. The single BPI item which inquires as to the degree of overall pain the patient experiences on average can be used, for instance. The BPI also asks the patient to rate how much pain has interfered with various general and specific activities as well as enjoyment of life.

Questions pertaining to patient-specific concerns can also be asked, in addition to inquiries encompassing the indicia addressed above.

CPA can be used in accordance with the present invention to treat castrated prostate cancer patients having any stage of prostate cancer, to improve the patients' overall quality of life.

A sufficient improvement in the quality of life of the patient can preferably be indicated, for example, by an increase in score of at least about 5 points on the FACT-G instrument the FACT-P instrument or a modified FACT-P instrument that asks additional questions relevant to an assessment of the patient's quality of life, e.g., relating to vasomotor hot flashes and/or any of the single item visual analogue questions and/or any other patient-specific concerns. To determine whether there is an increase in score, e.g., an improvement shown by an increase of at least 5 points, the patient is administered the test prior to the start of CPA treatment. The test is then administered during CPA treatment, for example, at a desired time in the course of treatment, or at any time during treatment to determine whether a desired measure of improvement has been reached. The score or scores obtained during or after CPA treatment are compared to the baseline score. The point scales of the FACT instruments represent raw scales, with zero representing worst quality of life and the highest score representing the best quality of life. The FACT-P and the modified FACT-P instrument each has a greater number of total points than does the FACT-G.

Preferably, the FACT-P instrument is used as a measure. Most preferably, a modified FACT-P instrument is used which includes further relevant questions such as those relating to hot flashes, the single-item questions and any further patient-specific concerns. More substantial improvement in quality of life is indicated by an increase in score of greater than 5 points on the FACT-G, FACT-P, or a modified FACT-P instrument.

It is deemed that an improvement in quality of life as measured by a given increase in score on a given quality of life assessing instrument when compared to baseline encompasses an equivalent improvement in a patient's quality of life with respect to the multidimensional aspects of quality of life in accordance with the present invention.

While it has been noted that vasomotor symptoms in castrated prostatic cancer patients are likely responsible for loss of sleep and the resultant symptoms, it is recognized that CPA in accordance with the present invention is also effective to improve the quality of life as defined above for castrated prostatic cancer patients who do not necessarily experience vasomotor hot flashes or who do not experience them to the extent that sleep is impaired. Also, patients need not experience bone pain or not to the extent that treatment of the pain alone is desired. For example, it is recognized that CPA administered at 25 mg to 150 mg per day in accordance with the present invention can be effective to alleviate symptoms of anxiety and associated symptoms in castrated prostatic cancer patients. Additional or alternative aspects of quality of life can also be favorably impacted such that an overall improvement in quality of life results.

The dosage is generally administered once per day, which is favorable in terms of patient compliance. Other dosage regimes such as twice a day administration may be implemented. The solid oral dosage is preferably formulated as 50 mg CPA. Other dosage amounts, e.g., a 100 mg or 25 mg oral dose of CPA, may be formulated. The dosage form is preferably a tablet. Other dosage forms such as capsules are contemplated.

Alternatively, CPA can be provided in other dosage forms such as a liquid oral dosage, an injectible depot, intranasal or a transdermal delivery system, for example, as a patch. The amount of CPA provided in each dosage form would provide equivalent blood levels of CPA as does from 25 mg to 150 mg solid oral dosage form of CPA.

When hot flashes are well managed or eliminated by a given dosage of CPA per day, a lower dose of CPA per day can be administered. For example, a 150 mg/day dose can be reduced to 100 mg/day. A 100 mg/day dosage which manages or eliminates hot flashes and/or other symptoms can be reduced to 50 mg/day, etc. The use of CPA at the lower dosage levels, when effective, may be more desirable than higher doses for some patients.

CPA is preferably administered for at least 60 days for the patient to experience benefits with regard to the multidimensional aspects of quality of life and/or for palliative therapy over time. Longer terms are preferable, as discussed above. Continuous or intermittent therapy can be employed, continuous therapy being preferred in view of supplemental anti-cancerocidal effects, as well as the other favorable aspects of the therapy.

The treatment of advanced prostatic carcinoma is palliative and rarely curative. The primary aim of therapy besides prolongation of life is preservation of the quality of the patient's life for as long as possible. Palliative care is generally the active total care of patients whose disease is not responsive to curative treatment, e.g., for Stage C and D patients. The goal of palliative care is the achievement of the best possible quality of life for patients and their families. (World Health Organization: Cancer Pain Relief. World Health Organization, Geneva (1986)). Unlike disease-modifying therapies, palliative care is primarily focused on the comfort, functioning and quality of life of the patient and family. Palliative care becomes the sole model after patients enter a period when primary disease-modifying therapies are no longer effective, available or desired. Control of pain, of other symptoms, and of psychological, social and spiritual problems is paramount.

The quality of life dimensions discussed above apply to patients with advanced prostatic cancer. As part of a study of treatment decision making by men with metastatic prostate cancer, Clark, J. A. et al. (Soc. Sci. Med. October (1997); 45(8):1299–1309) identified three major domains of life quality: self-perceptions, anxiety about the effects of treatment, and concern with the process of decision making and treatment. Nine reliable and valid indicators of prostate cancer-related quality of life were reported as follows: body image, sexual problems, spouse affection, spouse worry, masculinity, cancer-related self-image, cancer distress, cancer acceptance, and regret of treatment decision. Moreover, these prostate cancer patients were said to perceive a number of important and psychosocial consequences of their treatment.

One or more of the FACT or other quality of life assessing instruments can be used to determine the effect of CPA treatment on the patient's quality of life for providing palliative treatment. Clark et al. discuss a disease and treatment sensitive health-related quality of life instrument. This instrument or a portion thereof, may also be of use in assessing quality of life in castrated prostatic cancer patients, particularly those whose cancer is metastatic. Preferably, the FACT-P or modified FACT-P instrument is used.

It is recognized that CPA administered in accordance with the present treatment, provides an important palliative treatment that addresses a wide range of multidimensional factors affecting the overall quality of life of these advance stage patients. For example, CPA can reduce the incidence of pain and hot flashes, as well as psychological distress and functional impairment. It also can elevate mood. Treatment can result in an increase in weight, and antiandrogenic effects may supplement cancerocidal treatment with minimal side effects. Social/family well-being of the patient can improve. The effect of CPA on multidimensional aspects of quality of life contributes to the benefit to the patient with respect to their overall quality of life.

It is also recognized that CPA in combination with a low dose estrogen is useful in treating castrated prostatic cancer patients for vasomotor hot flashes as well as to improve the patients' quality of life. Patients having at least 6 hot flashes per day and patients diagnosed by a physician as experiencing hot flashes warranting treatment can benefit. A useful estrogen of the combination can be DES. Dosages in accordance with the present invention are from 25 mg to 150 mg CPA combined with about 0.1 mg DES per day. Dosages of from 50 mg CPA/0.1 mg DES to 100 mg CPA/0.1 mg DES are preferred. Treatment duration as well as other parameters are as discussed above for CPA alone. It is recognized that CPA/DES in combination can have a synergistic effect on vasomotor hot flushes and on improvement in quality of life.

It is also recognized that CPA can be used in combination with the estrogen chlorotrianisene to treat castrated prostatic cancer patients for vasomotor hot flushes as well as to improve the patients' quality of life. Patients having at least 5 hot flashes per day and those diagnosed by a physician as having hot flashes warranting treatment can benefit. Dosages in accordance with the present combination are from 25 mg to 150 mg CPA combined with from about 12 mg to about 25 mg chlorotrianisene per day. Dosages of 50 mg CPA or 100 mg CPA with from about 12 mg to about 25 mg chlorotrianisene are preferred. It is recognized that chlorotrianisene in the combination provides an effective treatment with low associated toxicity.

Other estrogens can be used, e.g., conjugated estrogens such as Premarin®. Synthetic conjugated estrogens may also be used.

A combination formulation of CPA with a low dose estrogen can be administered as a combined formulation or as two separate dosage units.

Castrated prostatic cancer patients undergoing treatment with CPA in accordance with the present invention can begin taking a low dose estrogen with their CPA therapy at any time. Commencing combination therapy prior to six months from the start of CPA administration may be particularly beneficial as it could alleviate any potential weakening of the antigonadotropic effect of CPA.

EXAMPLE 1

A castrated prostatic cancer patient experiencing approximately 6 hot flashes per day is administered 100 mg CPA once per day (two 50 mg tablets) for sixty days.

EXAMPLE 2

A castrated prostatic cancer patient experiencing approximately 10 hot flashes per day is administered 25 mg CPA per day for 180 days.

EXAMPLE 3

A castrated prostatic cancer patient experiencing 22 hot flashes per day is administered 100 mg CPA per day for about 6 months.

EXAMPLE 4

A castrated prostatic cancer patient experiencing hot flashes that the patient rates as mostly at least moderate, is administered 50 mg CPA per day for over one year.

EXAMPLE 5

A Stage D castrated prostatic cancer patient is administered 50 mg CPA per day as palliative therapy.

EXAMPLE 6

A chemically castrated prostatic cancer patient experiencing hot flashes is administered 100 mg per day for 1.5 years.

EXAMPLE 7

An orchiectomized prostatic cancer patient is administered 50 mg per day CPA to reduce hot flashes and to improve overall quality of life.

EXAMPLE 8

An orchiectomized prostatic cancer patient is administered 25 mg per day CPA to improve the overall quality of life of the patient.

EXAMPLE 9

A castrated prostatic cancer patient experiencing 8 hot flashes per day is administered 100 mg CPA once per day for 60 days. The patient does not take CPA for 35 days. CPA administration is then reinstituted, for another 30 days.

EXAMPLE 10

A castrated prostatic cancer patient experiencing hot flashes is administered 100 mg CPA per day. Administration continues after 60 days for at least until the patient's hot flashes are decreased and the patient's score on a modified FACT-P instrument that has questions in addition to the FACT-P instrument relating to hot flashes, increases by at least 5 points compared to the score obtained prior to the start of CPA treatment.

EXAMPLE 11

A castrated prostatic cancer patient is administered 50 mg CPA per day. Administration continues for at least until the patients' score on the FACT-P instrument increases by at least 5 points from the score obtained prior to the start of CPA treatment.

EXAMPLE 12

A castrated prostatic cancer patient experiencing approximately 12 hot flashes per day is given 50 mg CPA in combination with 0.1 mg DES for about 10 months.

EXAMPLE 13

A castrated prostatic cancer patient diagnosed with hot flashes warranting treatment is given 100 mg CPA in combination with 12 mg chlorotrianisene per day for about 6 months.

EXAMPLE 14

A castrated prostatic cancer patient is given 25 mg CPA in combination with 25 mg chlorotrianisene per day for at least until the patients' score on the FACT-P instrument is increased by 5 points compared to the score obtained prior to the start of CPA treatment.

What is claimed is:

1. In a method for treating hot flashes in a castrated prostatic cancer patient diagnosed with hot flashes warranting treatment, the improvement comprising administering to said patient a hot flash treating amount of from 25 mg to 100 mg cyproterone acetate per day in a solid oral dosage form for at least sixty days.

2. The method according to claim 1 wherein the administering is continuous.

3. The method according to claim 1 wherein the administering is continuous for at least sixty days and intermittent thereafter.

4. The method according to claim 1 wherein the administering is for at least about 6 months.

5. The method according to claim 4 wherein the administering is for from about 6 months to about 9 months.

6. The method according to claim 1 wherein the administering is for at least about 9 months.

7. The method according to claim 1 wherein the administering is for over 1 year.

8. The method according to claim 1 wherein the administering is for at least about 2 years.

9. The method according to claim 8 wherein the administering is for from about 2 to about 3 years.

10. The method according to claim 1 wherein the amount is from 50 mg to 100 mg cyproterone acetate per day.

11. The method according to claim 10 wherein the administering is for at least about 6 months.

12. The method according to claim 10 wherein the administering is for greater than one year.

13. The method according to claim 1 wherein the patient is a chemically castrated prostatic cancer patient.

14. The method according to claim 1 wherein the patient is an orchiectomized prostatic cancer patient.

15. The method according to claim 1 wherein the administering is once per day.

16. A method for treating hot flashes in a castrated prostatic cancer patient experiencing at least approximately 5 hot flashes per day, comprising administering to said patient a hot flash treating amount of from 25 mg to 100 mg cyproterone acetate per day in a solid oral dosage form for at least sixty days.

17. A method for treating hot flashes in a castrated prostatic cancer patient experiencing hot flashes, most of said hot flashes being rated as at least moderate in severity, comprising administering to said patient a hot flash treating amount of from 25 mg to 100 mg) cyproterone acetate per day in a solid oral dosage form for at least 9 months.

18. A method for improving the quality of life of a castrated prostatic cancer patient, the quality of life encompassing multidimensional aspects of physical well being, social/family well being, emotional well-being, functional well-being, psychosocial well-being, self perception and concerns that relate to prostate-cancer patients that include at least the factors of change in weight, appetite, urinary function, and hot flashes, the multidimensionial aspects being subjectively assessed by the patient, comprising administering to said patient a quality of life improving amount of from 25 mg to 150 mg cyproterone acetate per day in a solid oral dosage form for at least sixty days.

19. The method according to claim 18 wherein the castrated prostatic cancer patient experiences hot flashes prior to the administering of cyproterone acetate.

20. The method according to claim 18 wherein improvement in the patient's quality of life is measured by an increase in the patient's score of at least 5 points on a FACT-P instrument compared to the patient's score prior to cyproterone acetate treatment.

21. The method according to claim 18 wherein improvement in the patient's quality of life is measured by an increase in the patient's score of at least 5 points on a modified FACT-P instrument which includes in addition to the FACT-P questionnaire, statements for ranking which relate to hot flashes, where the increase in the patient's score from cyproterone acetate treatment is compared to the patient's score prior to cyproterone treatment.

22. The method according to claim 18 wherein the administering is once per day.

23. The method according to claim 18 wherein the patient is a chemically castrated prostatic cancer patient.

24. The method according to claim 18 wherein the patient is an orchiectomized prostatic cancer patient.

25. A method for providing palliative treatment to a castrated prostatic cancer patient having an advanced stage of cancer to improve the quality of life of the patient, quality of life encompassing multidimensional aspects of physical well being, social/family well being, emotional well-being, functional well-being, psychosocial well-being, self perception and concerns that relate to prostate cancer patients that include at least the factors of change in weight, appetite, urinary function, hot flashes, and anxiety about the effects of treatment, the multidimensional aspects being subjectively assessed by the patient, comprising administering to said patient a quality of life improving amount of from 25 mg to 150 mg cyproterone acetate per day in a solid oral dosage form for at least sixty days.

26. The method according to claim 23 wherein the castrated prostatic cancer patient experiences hot flashes prior to the administering of cyproterone acetate.

27. The method according to claim 23 wherein improvement in the patient's quality of life is measured by an increase in the patient's score of at least 5 points on a FACT-P instrument compared to the patients' score prior to cyproterone acetate treatment.

28. The method according to claim 23 wherein improvement in the patient's quality of life is measured by an increase in the patient's score of at least 5 points on a modified FACT-P instrument which includes in addition to the FACT-P questionnaire, statements for ranking which relate to hot flashes, where the increase in the patient's score from cyproterone acetate treatment is compared to the patient's score prior to cyproterone acetate treatment.

29. The method according to claim 23 wherein the administering is once per day.

30. The method according to claim 24 wherein the patient is a chemically castrated prostatic cancer patient.

31. The method according to claim 24 wherein the patient is an orchiectomized prostatic cancer patient.

* * * * *